(12) United States Patent
Ushiroda

(10) Patent No.: US 10,244,958 B2
(45) Date of Patent: *Apr. 2, 2019

(54) DEVICE FOR MEASUREMENT AND EVALUATION OF CARDIAC FUNCTION ON THE BASIS OF THORACIC IMPEDANCE

(71) Applicant: MEDICAL CORPORATION USHIRODA INTERNAL MEDICINE CLINIC, Iwaki-shi, Fukushima (JP)

(72) Inventor: Shinichi Ushiroda, Iwaki (JP)

(73) Assignee: MEDICAL CORPORATION USHIRODA INTERNAL MEDICINE CLINIC, Fukushima (JP)

( * ) Notice: Subject to any disclaimer, the term of this patent is extended or adjusted under 35 U.S.C. 154(b) by 50 days.

This patent is subject to a terminal disclaimer.

(21) Appl. No.: 15/381,795

(22) Filed: Dec. 16, 2016

(65) Prior Publication Data

US 2017/0143225 A1    May 25, 2017

Related U.S. Application Data

(63) Continuation of application No. PCT/JP2014/066906, filed on Jun. 25, 2014.

(51) Int. Cl.
*A61B 5/04* (2006.01)
*A61B 5/0456* (2006.01)
(Continued)

(52) U.S. Cl.
CPC .......... *A61B 5/04012* (2013.01); *A61B 5/044* (2013.01); *A61B 5/046* (2013.01);
(Continued)

(58) Field of Classification Search
None
See application file for complete search history.

(56) References Cited

U.S. PATENT DOCUMENTS 6,438,408 B1 *  8/2002  Mulligan ........... A61N 1/36564
                                                     600/510
6,738,667 B2 *  5/2004  Deno ................... A61N 1/3627
                                                     607/23
(Continued)

FOREIGN PATENT DOCUMENTS

EP   2 937 038 A1    10/2015
WO   2005/077260 A1   8/2005
WO   2014/102964      7/2014

OTHER PUBLICATIONS

Myocardial Contractility Is Not Constant During Spontaneous Atrial Fibrillation in Patients, Carl I.O. Brookes et al., 1998 American Heart Association, Inc., vol. 98, pp. 1762-1768, discussed in specification.

(Continued)

*Primary Examiner* — Eric D. Bertram
*Assistant Examiner* — Elizabeth K So
(74) *Attorney, Agent, or Firm* — Rankin, Hill & Clark LLP

(57) ABSTRACT

A cardiac function measurement and evaluation device is provided to measure and evaluate cardiac function in patients with atrial fibrillation, sinus arrhythmia, and the like, using thoracic impedance data and electrocardiogram data. By creating a two-dimensional scatter plot in which (dZ/dt)min values and preceding RR intervals (RR1) corresponding thereto, and the like obtained by thoracic impedance measurement, are plotted, it is possible to visually and easily evaluate the state of cardiac function in patients with atrial fibrillation and sinus arrhythmia. Using the measurement and evaluation device of the present invention makes it possible to perform examinations easily and repeatedly with less burden on patients. Therefore, it is possible to (Continued)

provide very useful information for diagnosing heart disease, selecting drugs, and the like.

11 Claims, 9 Drawing Sheets

(51) Int. Cl.
| | |
|---|---|
| *A61B 5/0428* | (2006.01) |
| *A61B 5/0432* | (2006.01) |
| *A61B 5/044* | (2006.01) |
| *A61B 5/00* | (2006.01) |
| *A61B 5/046* | (2006.01) |
| *A61B 5/0468* | (2006.01) |
| *A61B 5/053* | (2006.01) |
| *A61B 5/0295* | (2006.01) |

(52) U.S. Cl.
CPC .......... *A61B 5/0432* (2013.01); *A61B 5/0456* (2013.01); *A61B 5/0468* (2013.01); *A61B 5/04286* (2013.01); *A61B 5/0535* (2013.01); *A61B 5/7264* (2013.01); *A61B 5/0295* (2013.01)

(56) References Cited

U.S. PATENT DOCUMENTS

| | | | | |
|---|---|---|---|---|
| 7,031,765 | B2 * | 4/2006 | Ritscher | A61B 5/0464 |
| | | | | 600/518 |
| 9,560,983 | B2 * | 2/2017 | Ushiroda | A61B 5/0456 |
| 2005/0192488 | A1 * | 9/2005 | Bryenton | A61B 5/02055 |
| | | | | 600/301 |
| 2006/0247702 | A1 | 11/2006 | Stegemann et al. | |
| 2007/0043299 | A1 | 2/2007 | Wariar et al. | |
| 2010/0274141 | A1 | 10/2010 | Patangay et al. | |
| 2015/0327790 | A1 | 11/2015 | Ushiroda | |

OTHER PUBLICATIONS

Left ventricular beat to beat performance in atrial fibrillation: dependence on contractility, preload, and afterload, H.J. Muntinga et al., Heart (1999), vol. 82, pp. 575-580, discussed in specification.
Interval-Dependent Changes in Left Ventricular Contractile State in Lone Atrial Fibrillation and in Atrial Fibrillation Associated With Coronary Artery Disease, 1997 by Excerpta Medica, Inc., vol. 80, pp. 586-590, discussed in specification.
Determination of Cardiac Output in Man by Means of Impedance Plethysmography, Aerospace Medicine (1968), vol. 39(3), pp. 248-252, discussed in specification.
International Search Report, dated Jul. 29, 2014 (Jul. 29, 2014).
M. Risdal et al., "Examining the Potential of Using Thorax Impedance Measured by Automated External Defibrillators for Quantification of Circulation", Computers in Cardiology, 2005, Lyon, France, Sep. 25-28, 2005, Piscataway IEEE, NJ, USA, Sep. 25, 2005 (Sep. 25, 2005), pp. 809-812, XP010889962, DOI: 10.1109/CIC.2005.1588228 ISBN: 978-0-7803-9337-0, English text, 4 pages.
F.L. Meijler et al., "Computer Analysis of the PR Interval-Contractility Relationship during Random Stimulation of the Isolated Heart", Circulation Research, vol. 22, No. 5, May 1, 1968 (May 1, 1968), pp. 695-702, XP055377021, US ISSN: 0009-7330, DOI: 10.1161/01.RES.22.5.695, English text, 9 pages.
European Search Report, dated Jun. 8, 2017, 11 pages.

* cited by examiner

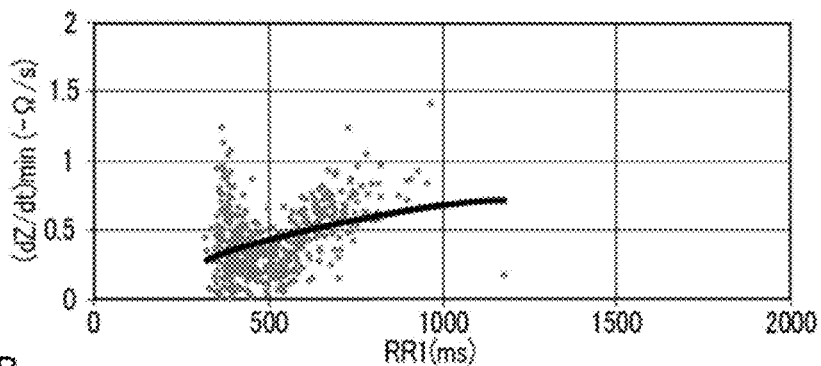
FIG.3A (dZ/dt)min METHOD (BEFORE TREATMENT)
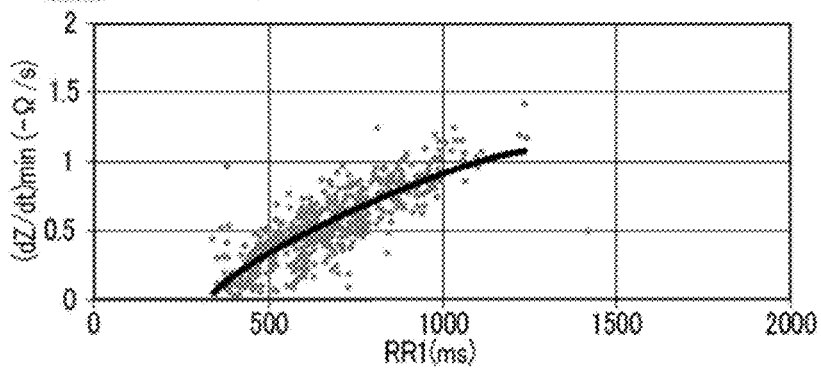
FIG.3B (dZ/dt)min METHOD (AFTER TREATMENT)
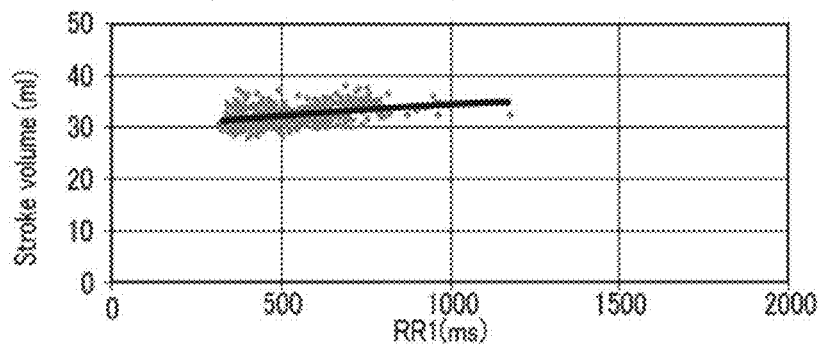
FIG.3C SV METHOD (BEFORE TREATMENT)
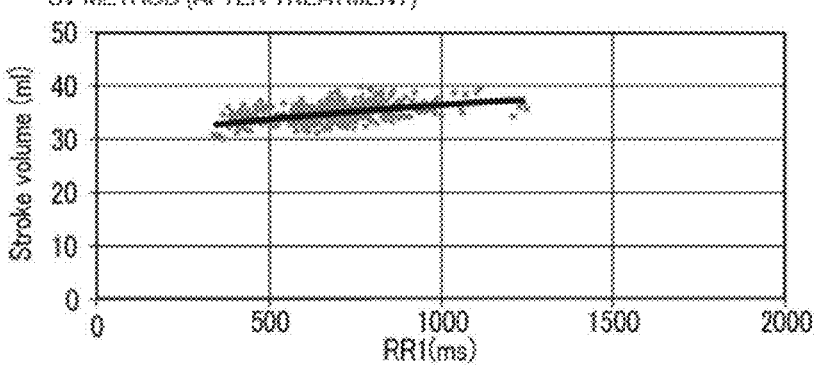
FIG.3D SV METHOD (AFTER TREATMENT)

FIG. 6A HEART FAILURE WITH ATRIAL FIBRILLATION
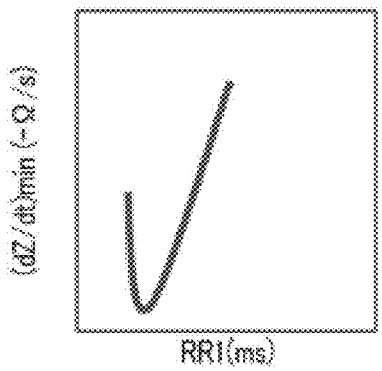
FIG. 6B GOOD CARDIAC FUNCTION IN ATRIAL FIBRILLATION
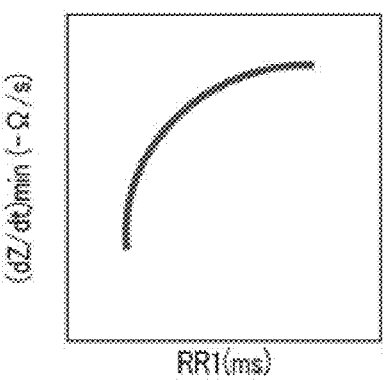
FIG. 6C NORMAL SINUS RHYTHM
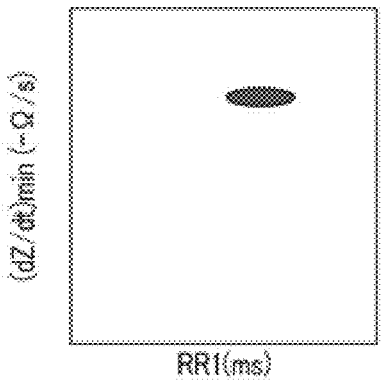

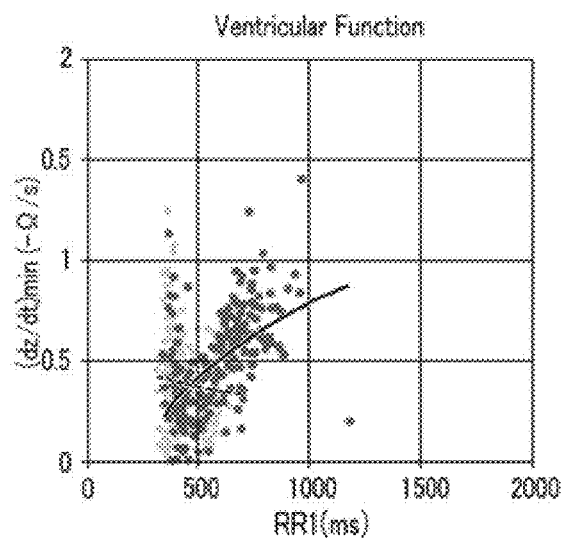
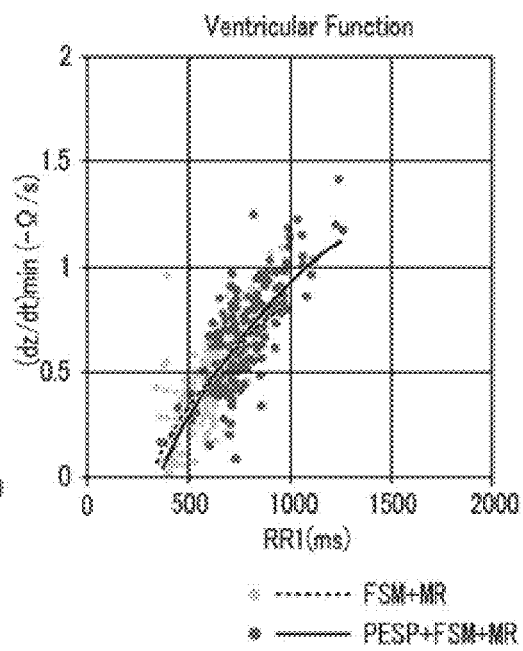
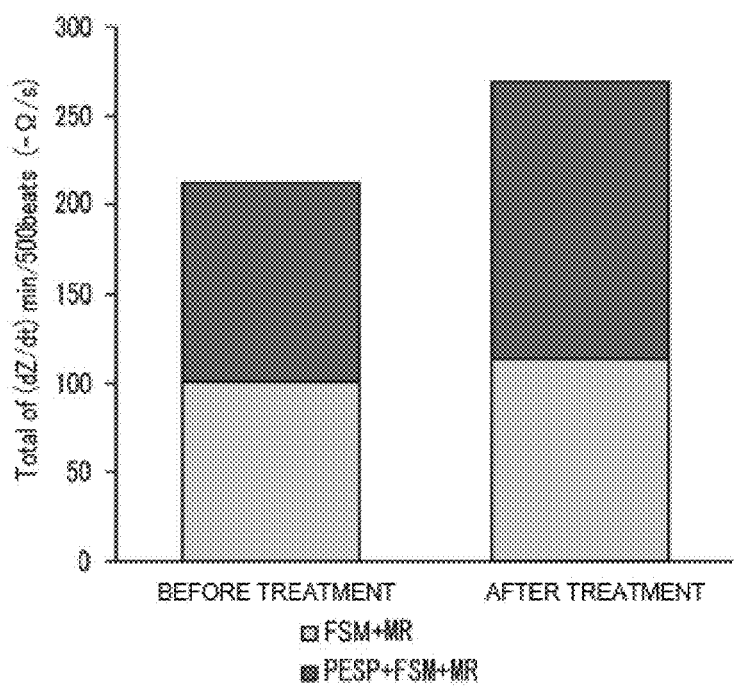
FIG.7A BEFORE TREATMENT
FIG.7B AFTER TREATMENT
FIG.7C

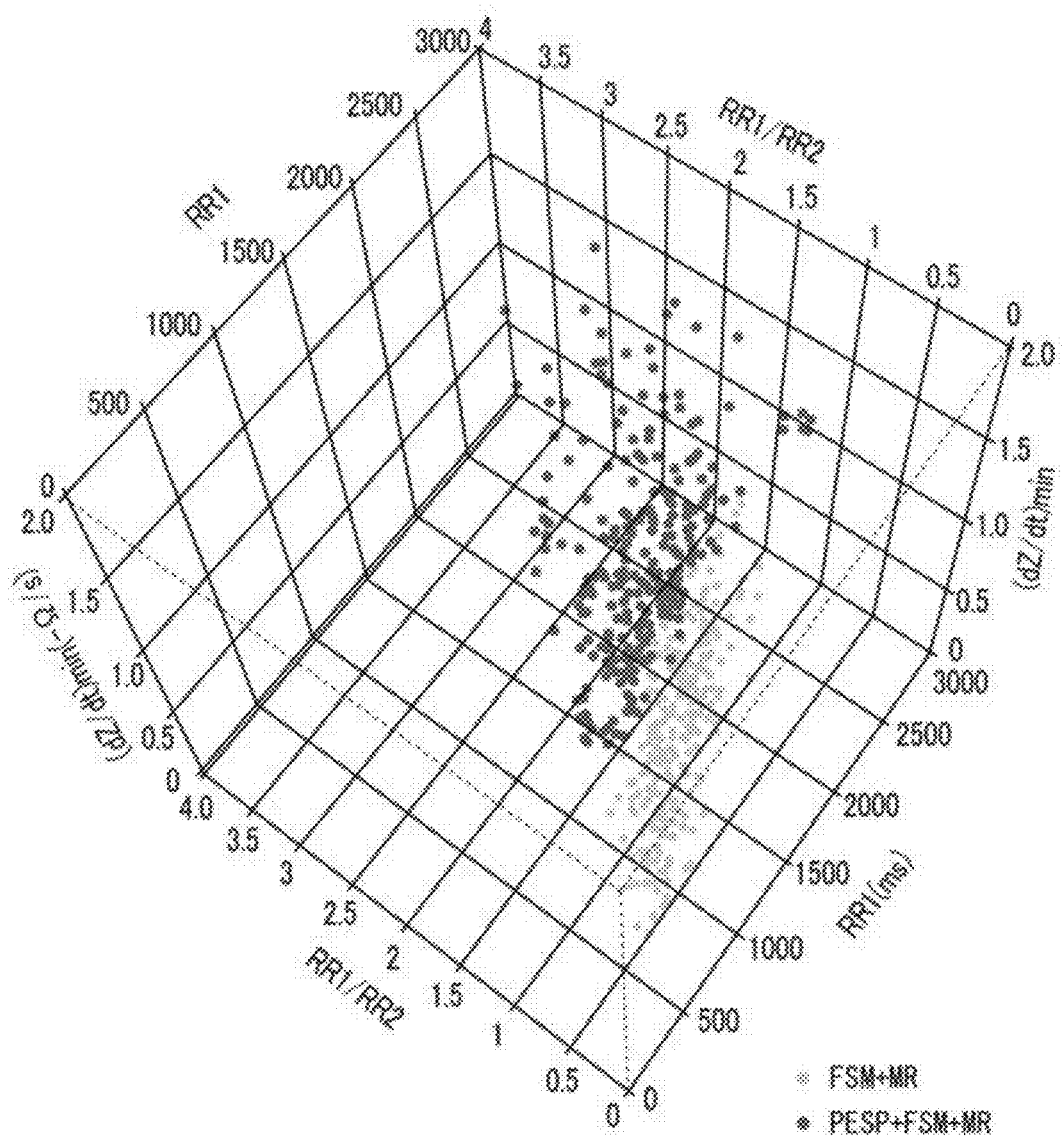

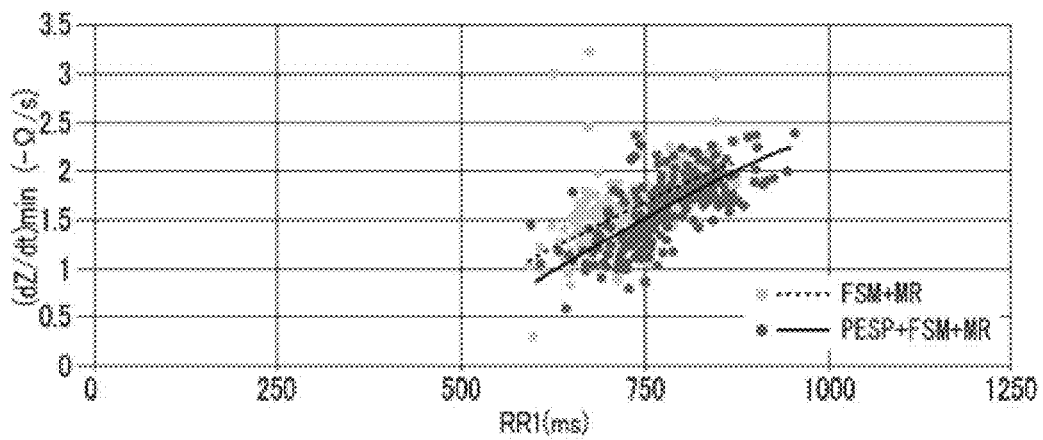
FIG. 9A VENTRICULAR FUNCTION
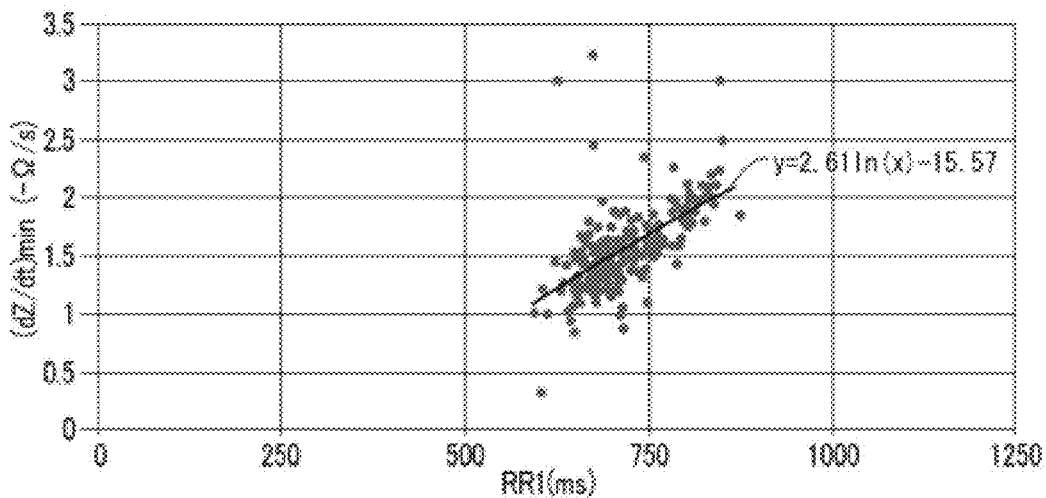
FIG. 9B FRANK-STARLING MECHANISM AND MECHANICAL RESTITUTION
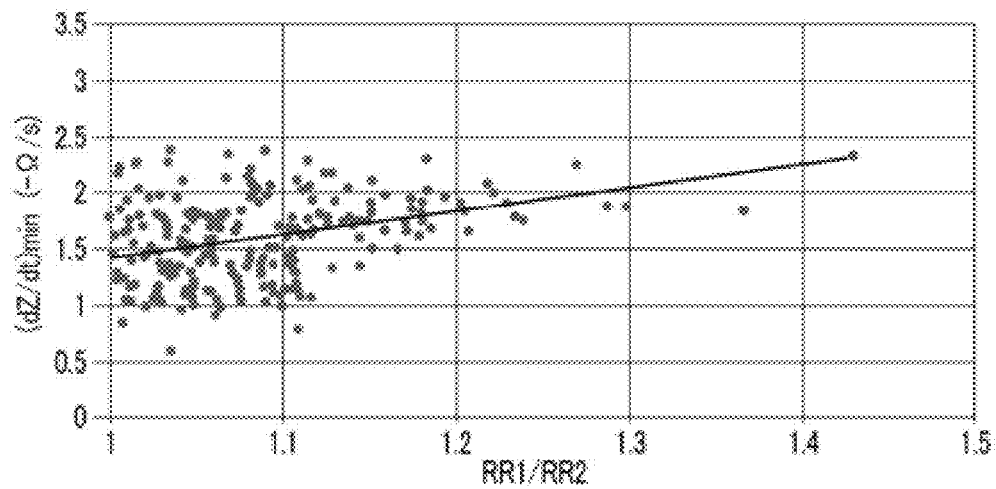
FIG. 9C POSTEXTRASYSTOLIC POTENTIATION

DEVICE FOR MEASUREMENT AND EVALUATION OF CARDIAC FUNCTION ON THE BASIS OF THORACIC IMPEDANCE

TECHNICAL FIELD

The present invention relates to a device for measuring thoracic impedance and electrocardiogram (ECG), and evaluating cardiac function based on the obtained data. In particular, the present invention relates to a device for analyzing cardiac function to objectively determine diagnosis of cardiac function in patients with atrial fibrillation or sinus arrhythmia, selection of therapeutic drugs, therapeutic effects, and performing evaluation.

BACKGROUND ART

Patients with cardiovascular disease are increasing in association with the aging society. In cardiovascular disease, early detection and follow-up in treatment are important as well as other diseases, and periodic examination of cardiovascular function is needed.

In cardiovascular disease, morbidity of atrial fibrillation increases along with aging. An epidemiological study shows that the prevalence thereof increases sharply over the age of 70, and it reaches 4% to 8% in 70's, and reaches 10% in 80's. Further, it has been indicated that patients with atrial fibrillation have a high risk of left atrial thrombi which may flow out from the heart and occlude cerebral vessels to thereby cause cardioembolic stroke. Accordingly, by means of positive use of anticoagulants for preventing cardioembolic stroke in recent years, treatment of embolism associated with atrial fibrillation has been improved dramatically.

On the other hand, in patients with atrial fibrillation, heart rhythm is irregular and tachycardia often occurs, which decreases the cardiac output and worsens the cardiac function. Accordingly, in order not to worsen the cardiac condition, a treatment for controlling the irregular heart rate appropriately has been performed. However, the results of a mega-scale clinical trial demonstrated that there were no differences in life prognosis between a group of patients in which the heart rate was strictly controlled less than 80 per minute and a group of patients in which the heart rate was controlled in a non-strict manner less than 110 per minute. Then, it is considered to be meaningless to give treatment to a patient with atrial fibrillation by using heart rate as an index. Nowadays, medical treatment is given based on symptoms complained by a patient such as palpitation, a feeling of dyspnea, and a feeling of fatigue.

As patients with atrial fibrillation are increasing along with the rapid aging of society, patients with dementia are also increasing. Further, it has been reported that patients with atrial fibrillation have a risk of dementia about 1.4 times. In such a situation, it is considered to be problematic to give treatment based on only symptoms complained by elderly patients. This also applies to pediatric patients who are not able to explain symptoms accurately. Thus, it has been required to objectively perform diagnosis, medical treatment, and follow-up by using a cardiac function index which is an essential index for treatment of atrial fibrillation, instead of a therapeutic strategy based on subjective symptoms complained by a patient.

CITATION LIST

Non Patent Literature

Non Patent Literature 1: C. I. O. Brookes et al., Circulation (1998) Vol. 98, p. 1762-1768

Non Patent Literature 2: H. J. Muntinga, et al., Heart (1999), Vol. 82, p. 575-580

Non Patent Literature 3: F. Schneider et al., Am J Cardiol. (1997), Vol. 80, p. 586-590

Non Patent Literature 4: A. Harley & J. C. Greenfield Jr., Aerospace Medicine (1968), Vol. 39(3), p. 248-252

SUMMARY OF INVENTION

Technical Problem

In general, ECG is used for measuring the cardiac function in a medical examination or the like. ECG is a way to measure the cardiac electrical phenomenon from the body surface, and is used for diagnosing an anatomical abnormality of the heart such as cardiomegaly, angina, or myocardial infarction, and a rhythm disorder such as arrhythmia. Concretely speaking, such diagnosis can be made according to the waveform and the rhythm of an ECG recorded by ECG measurement.

On the other hand, it is impossible to measure cardiac function in heart failure, that is, strength of cardiac contractile force by the ECG. Generally, in order to determine cardiac function, it is necessary to measure cardiac output (CO). Cardiac output is calculated as a product of heart rate (HR) and stroke volume (SV) (CO=HR×SV) per minute.

In the case of healthy heart, when the heart rate is faster during exercise, the stroke volume is maintained because the cardiac contractile force increases, so that the cardiac output is increased by the exercise intensity. On the other hand, in the case of diseased heart such as heart failure, when the heart rate is faster during exercise, the stroke volume decreases and there is no correlation between the heart rate and the cardiac output because the cardiac contractile force is weakened. This leads to symptoms such as shortness of breath during exercise and a feeling of fatigue. Therefore, in the case of diseased heart such as heart failure, it is necessary to directly measure cardiac function such as a stroke volume and cardiac output, rather than the heart rate measured by ECG.

However, in the case of atrial fibrillation in which the rhythm is irregular, ventricular contraction occurs irregularly, so that the stroke volume is not constant. Therefore, it is impossible to evaluate cardiac function correctly by using the stroke volume. Further, the cardiac output, which is the product of values of heart rate per minute and stroke volume, cannot lead to an accurate evaluation of the cardiac function because the heart rate and the stroke volume per minute take dispersed values. In view of the above, in the case of atrial fibrillation, a ventricular function curve representing changes in the stroke volume due to irregular heartbeats is considered to be useful as an index of cardiac function, rather than the cardiac output and the stroke volume.

To obtain a ventricular function curve which is a cardiac function index of atrial fibrillation, four examinations of cardiac function, namely cardiac catheterization, cardiac radionuclide examination, echocardiography, and thoracic impedance method, have been performed as representative methods (See Non-Patent Literatures 1 to 4).

Cardiac catheterization is a most accurate and reliable test among the examinations of cardiac function. However, it is an extremely invasive test in which a catheter is directly inserted into the aorta with administration of a contrast medium. As an inpatient take risks of pain, bleeding, infection, and the like, such a examination cannot be performed easily and repeatedly.

The test of cardiac function using cardiac radionuclide examination has a high accuracy. However, since a radioactive agent is used as a tracer, a special examination room is required, so that available hospitals are limited. Further, because of using a radioactive tracer, it cannot be performed repeatedly on a patient for follow-up and confirmation of therapeutic effect due to a problem of exposure to radiation.

As cardiac catheterization and cardiac radionuclide examination require inpatient facilities, large medical apparatus, and the like, such tests can be performed in only limited hospitals. Further, due to problems of a physical burden on the patient and exposure to radiation, it is impossible to perform such tests if a patient needs repetition tests such as follow-up.

Echocardiography is a non-invasive test, which can be performed easily in a short period of time without a need of large apparatus. However, this examination involves a problem in reproducibility, because some area may not be imaged due to bones or air in the lung, and further, the test depends on the skill of the echo operator. Thus, it is considered not to be suitable for monitoring slight changes in the cardiac function (ventricular function curve).

Thoracic impedance method is a test by which cardiac output and a stroke volume can be measured non-invasively in a short period of time, so that the test can be performed repeatedly. However, since stroke volume in atrial fibrillation has a large margin of error, evaluation of cardiac function and monitoring of treatment course in atrial fibrillation using a ventricular function curve applying stroke volume obtained by the impedance method have not been performed until today, for about forty years.

As described above, every test has drawbacks mentioned above. A test by which cardiac function (ventricular function curve) can be measured repeatedly and non-invasively in a short period of time with high sensitivity has been desired for diagnosing severity of atrial fibrillation and medical treatment.

In view of the above, an object of the present invention is to provide a device by which a test can be performed easily and repeatedly with less physical burden on a patient, and in which slight changes in cardiac function can be detected with high sensitivity. By using the device of the present invention, a highly accurate ventricular function curve of atrial fibrillation can be created, which enables treatment to be performed on a patient with atrial fibrillation based on objective data.

Further, another object is to provide cardiac function data in a visually displayed manner so as to allow easy visual understanding of pathophysiological mechanisms of ventricular contraction, which is required for determining the course of cardiac function and a choice of effective medication in a patient with atrial fibrillation. In addition, another object is to provide a device which does not require skill in examination technique for data acquisition and analysis.

The inventor of the present invention has found a novel and highly sensitive method of cardiac function analysis. The method includes, using the above-described thoracic impedance method which is a non-invasive test placing less burden on a patient and allowing the test to be performed repeatedly, performing arithmetic processing based on obtained measurement values, and creating and displaying a graph by connecting a peak flow velocity of blood ejected from the ventricles (hereinafter also referred to as (dZ/dt)min) to preceding RR intervals.

Furthermore, the inventor has also found that three ventricular contractile mechanisms, which are known as Frank-Starling mechanism (FSM), mechanical restitution (MR), and postextrasystolic potentiation (PESP), can be easily analyzed and displayed based on the analysis method, and the pathophysiological mechanisms of cardiac function can be understood in more detail. The device of the present invention is a device for performing analysis of such a cardiac function mechanism.

By using the device of the present invention, it is possible to easily find out a patient with heart failure associated with atrial fibrillation. Furthermore, an evaluation of severity of the condition, a selection of therapeutic drugs, an assessment of effects of medical treatment, monitoring of treatment course, and the like, can be easily and objectively performed. Thus, an appropriate treatment can be applied.

Solution to Problem

A device for measuring and evaluating cardiac function in a subject, according to the present invention, is characterized as including thoracic impedance measuring unit; electrocardiogram measuring unit; arithmetic unit; storage unit; and display unit, wherein the thoracic impedance measuring unit includes drive electrodes for applying an electrical current, and receive electrodes for extracting an impedance signal, and measures a plurality of continuous sets of thoracic impedances; the electrocardiogram measuring unit includes a signal detection module that detects electrocardiogram signals from electrodes applied to the subject, and measures a plurality of continuous sets of electrocardiogram signals; the arithmetic unit calculates (dZ/dt)min values of the plurality of continuous sets of thoracic impedances measured by the thoracic impedance measuring unit, and preceding RR intervals (RR1) from R waves of the electrocardiogram signal obtained by the electrocardiogram measuring unit; the storage unit stores as a data set: a (dZ/dt)min value of each of the sets of thoracic impedance data corresponding to an RR1 value of each of the calculated plurality of continuous sets of electrocardiogram data, and the display unit displays each of the (dZ/dt)min values corresponding to each of the RR1 values.

A device in which a thoracic impedance measuring device and an electrocardiogram measuring device are combined has been in the market as a cardiac function measuring device. However, since there has been no analysis method by means of linking both measurement values, the results have been displayed as independent test results of thoracic impedance and ECG, and the respective measurement values have been used as independent test results for diagnosis by medical doctors.

However, the inventor of the present invention has found that cardiac function can be analyzed and evaluated in detail by performing analysis of linking (dZ/dt)min values which are measurement values of thoracic impedance, to preceding RR intervals (RR1) which are measurement values of ECG corresponding thereto.

In order to achieve such a method, it is indispensable to calculate (dZ/dt)min values from continuous sets of thoracic impedance data and preceding RR intervals (RR1) from continuous sets of ECG data, extract a preceding RR interval (RR1) corresponding to each (dZ/dt)min value as a data set, and analyze a plurality of continuous data sets.

The cardiac function measurement and evaluation device of the present invention is characterized in that the display unit displays respective (dZ/dt)min values of the thoracic impedance data corresponding to the respective RR1 values of the obtained of electrocardiogram data as a scatter plot.

By displaying them as a scatter plot, since cardiac function of a subject can be captured visually, cardiac function can be evaluated easily. Consequently, not only medical doctors but also medical technicians are able to perform the evaluation without a skill.

The cardiac function measurement and evaluation device of the present invention is characterized in that an approximate curve is obtained from the scatter plot of the (dZ/dt)min values of the thoracic impedance data corresponding to the respective RR1 values, and is displayed.

By obtaining an approximate curve and displaying it, slight changes in cardiac function can be detected from the slope thereof, which is useful for evaluation of the therapeutic effect and the like.

The cardiac function measurement and evaluation device of the present invention is characterized in that pre-preceding RR intervals (RR2) and RR1/RR2 values are calculated by the arithmetic unit from a plurality of continuous sets of electrocardiogram data obtained by the electrocardiogram measuring unit and (dZ/dt)min values corresponding to those are displayed.

By calculating RR1/RR2 values by the arithmetic unit from preceding RR intervals (RR1) and pre-preceding RR intervals (RR2), it is possible to extract (dZ/dt)min values involved in postextrasystolic potentiation (PESP) and (dZ/dt)min values related to Frank-Starling mechanism (FSM) and mechanical restitution (MR) not involved postextrasystolic potentiation. Consequently, cardiac function can be analyzed and evaluated in more detail.

The cardiac function measurement and evaluation device of the present invention is characterized in that (dZ/dt)min values corresponding to RR1/RR2≤1 are extracted as (dZ/dt)min values (FSM+MR) in which PESP is not involved, (dZ/dt)min values corresponding to RR1/RR2>1 are extracted as (dZ/dt)min values (PESP+FSM+MR) in which PESP is involved, and the respective (dZ/dt)min values corresponding to the RR1 values are displayed distinguishably as a scatter plot.

Using the scatter plot showing the degrees of involvement of three ventricular contractile mechanisms in cardiac function associated with the preceding RR intervals, it is possible to easily and visually evaluate the severity of disease condition, the clinical course, and the like.

The cardiac function measurement and evaluation device of the present invention is characterized in that the respective approximate curves are obtained from the scatter plot of the respective (dZ/dt)min values of the thoracic impedance data extracted as the FSM+MR and the PESP+FSM+MR, and then they are displayed.

By obtaining the respective approximate curves of the (dZ/dt)min values (FSM+MR) in which PESP is not involved and the (dZ/dt)min values (PESP+FSM+MR) in which PESP is involved, the slope of the curves makes it possible to evaluate the degree of contribution of the mechanisms related to cardiac function such as preload, afterload, myocardial contractility, and a degree of sympathetic nerve activity. Moreover, the result can be used for selecting therapeutic drugs, evaluation of therapeutic effect, and the like.

The cardiac function measurement and evaluation device of the present invention is characterized in that (dZ/dt)mim values corresponding to RR1/RR2≤1 are extracted as (dZ/dt)min values (FSM+MR) in which PESP is not involved, (dZ/dt)min values corresponding to RR1/RR2>1 are extracted as (dZ/dt)mim values (PESP+FSM+MR) in which PESP is involved, and a total of the respective (dZ/dt)mim values are calculated.

Obtaining a total of FSM+MR and PESP+FSM+MR makes it possible to estimate a degree of contribution of pathophysiological mechanisms in the recovery process of cardiac function, which cannot be estimated by changes of the patterns of plots and the correlation of approximate curves. Therefore, it is possible to choose drugs and determine administration periods of the drugs based on the above-described total.

The cardiac function measurement and evaluation device of the present invention is characterized in that (dZ/dt)min values corresponding to RR1/RR2≤1 are extracted as (dZ/dt)min values (FSM+MR) in which PESP is not involved, (dZ/dt)min values corresponding to RR1/RR2>1 are extracted as (dZ/dt)min values (PESP+FSM+MR) in which PESP is involved, and the respective corresponding RR1, RR1/RR2, and (dZ/dt)min values are displayed as a three-dimensional scatter plot.

By displaying simultaneously as the three-dimension, the plotted groups representing FSM+MR and PESP+FSM+MR can be displayed without being overlapped. Consequently, slight changes in cardiac function can be detected more accurately.

The cardiac function measurement and evaluation device of the present invention is characterized in that (dZ/dt)min values corresponding to RR1/RR2>1 are extracted as (dZ/dt)min values (PESP+FSM+MR) in which PESP is involved, and are displayed as a scatter plot corresponding to the respective RR1/RR2 values.

By displaying (dZ/dt)min values (PESP+FSM+MR) corresponding to respective RR1/RR2 values associated with RR1/RR2>1 as a scatter plot, the degree of involvement of PESP in cardiac function can be estimated easily and visually. Therefore, it is useful for prompt evaluation of severity of the condition, treatment course, and the like.

The cardiac function measurement and evaluation device of the present invention is characterized in that an approximate straight-line is obtained from the scatter plot of the respective (dZ/dt)min values of the thoracic impedance data extracted as the PESP+FSM+MR, and the line is displayed.

By calculating the slope of the approximate straight-line, the degree of cardiac sympathetic nerve activity can be evaluated.

The cardiac function measurement and evaluation device of the present invention is characterized in that the storage unit is allowed to store standard data, and the arithmetic unit includes a determination module that compares obtained data of the subject with the standard data and determines cardiac function.

By allowing the storage unit to store standard data, diagnostic criteria for disease can be obtained. Furthermore, since a determination module that performs comparison with the standard data is provided, it is possible to perform comparison with the subject, and also automatically perform initial screening of the subject's disease before a doctor's assessment. Further, since a determination module that performs comparison with the standard data is provided, it is possible to make accurate determination without the need for skills of the examiner.

The cardiac function measurement and evaluation device of the present invention is characterized in that the determination module further performs comparison with past data of same subject stored in the storage unit, and determines the course of cardiac function.

When compared with analytical results from measurements in the same patient, it is possible to easily evaluate the clinical course of patient and help in the therapeutic strategy for medication and the like.

BRIEF DESCRIPTION OF DRAWINGS

FIG. 3A shows a two-dimensional scatter plot and a ventricular function curve created from thoracic impedance data before treatment by the (dZ/dt)min method using a device of the present invention.

FIG. 3B shows data after treatment by the same (dZ/dt) min method.

FIG. 3C shows a two-dimensional scatter plot created by a conventional SV method in the same case and a ventricular function curve obtained as an approximate curve using the respective sets of data before treatment.

FIG. 3D shows data after treatment by the same SV method.

FIG. 6A is a diagram schematically showing the representative of cardiac function displayed by a two-dimensional scatter plot created by the (dZ/dt)min method, in which heart failure with atrial fibrillation is shown.

FIG. 6B is a diagram schematically showing improved cardiac function in atrial fibrillation.

FIG. 6C is a diagram schematically showing normal sinus rhythm.

FIG. 7A is a diagram showing a curve of Frank-Starling mechanism (FSM) and mechanical restitution (MR), and a curve in which postextrasystolic potentiation (PESP) is added thereto, before treatment.

FIG. 7B is a diagram showing the same case after treatment.

FIG. 7C is a diagram showing the total of the degree of involvement of each mechanism.

FIG. 8 shows a three-dimensional simultaneous scatter plot in which Frank-Starling mechanism (FSM), mechanical restitution (MR), and postextrasystolic potentiation (PESP) are involved.

FIG. 9A is a diagram showing ventricular function of a case of an application to pediatric respiratory sinus arrhythmia besides atrial fibrillation.

FIG. 9B is a diagram showing Frank-Starling mechanism (FSM) and mechanical restitution (MR) in the same case.

FIG. 9C is a diagram showing postextrasystolic potentiation in the same case.

DESCRIPTION OF EMBODIMENTS

Figure 1:
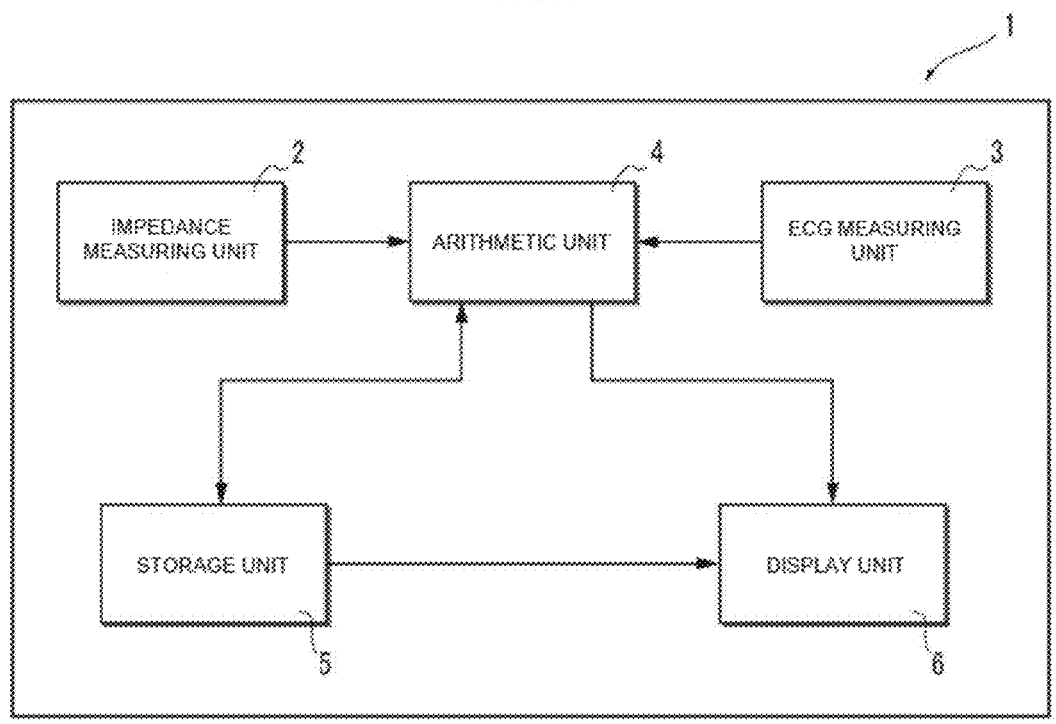
FIG. 1 is a diagram showing a schematic configuration of a device for measurement and evaluation of cardiac function.

Hereinafter, a device of the present invention will be described with reference to the drawings. FIG. 1 shows a schematic configuration of a device 1 for measurement and evaluation of cardiac function in the present invention. The device 1 for measurement and evaluation of cardiac function includes an impedance measuring unit 2 and an electrocardiogram measuring unit 3. Electrical signals detected by the respective measurement units of the impedance measuring unit 2 and the electrocardiogram measuring unit 3 are transmitted to an arithmetic unit 4. After arithmetic processing described below, the electrical signals are stored in a storage unit 5, and displayed on a display unit 6.

While devices equipped with an impedance measuring unit and an electrocardiogram measuring unit have been in the market, the measured impedance data and electrocardiogram data have been used independently for evaluating cardiac function.

The inventor of the present invention has found the relationship between an interval of an R wave and an R wave of electrocardiogram data measured by the electrocardiogram measuring unit and a dZ/dt waveform of the first derivative of AZ of impedance data, which is useful for evaluating cardiac function. The outline of the method for evaluating cardiac function in the present invention will be described first, then the details of the device will be described.

Figure 2A:
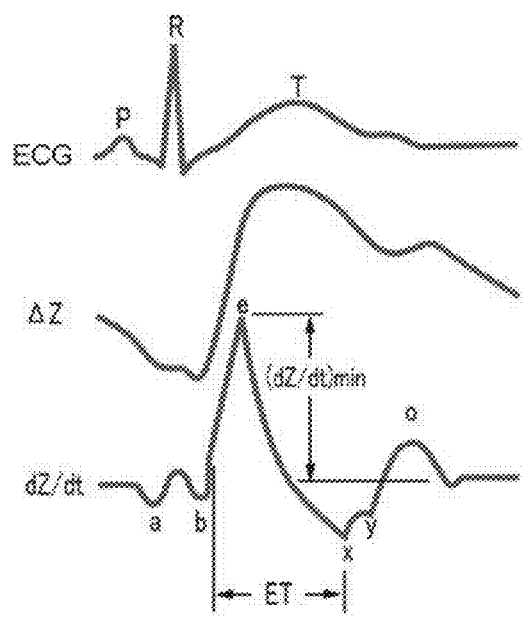
FIG. 2A is a diagram showing a typical ECG, a change in thoracic impedance AZ, and a dZ/dt waveform of the first derivative thereof.

FIG. 2A shows a typical electrocardiogram and thoracic impedance waveform. A cardiac cycle is composed of a systole and a diastole. Diastole is a period characterized by beginning of increasing ventricular cavity (left ventricle and right ventricle) and flowing blood from the atriums (left atrium and right atrium) into the ventricles, then resulting in ventricules filled with blood. Systole is a period characterized by beginning of ventricular contraction and ejecting the blood filled in the ventricles to the aorta and the pulmonary artery. A wave having the highest height that appears during systole in the electrocardiogram waveform is called an R wave (see electrocardiogram in FIG. 2A).

In FIG. 2A, AZ represents an impedance change in the thorax, and dZ/dt represents a waveform of the first derivative of AZ. In dZ/dt, waves of a, b, e, x, y, and o are recognized. The a-wave is associated with atrial contraction, the b-wave is associated with the onset of ejection of blood from the ventricles to arteries. The e-wave, that is, (dZ/dt) min, represents a peak blood flow velocity of the blood ejected from the ventricles, the x-point corresponds to the closure of the aortic valve, and the y-point corresponds to the closure of the pulmonary valve. Further, the o-point is associated with the period of opening of the mitral valve. It should be noted that in atrial fibrillation, the a-wave does not appear because of a loss of atrial contraction.

Figure 2B:
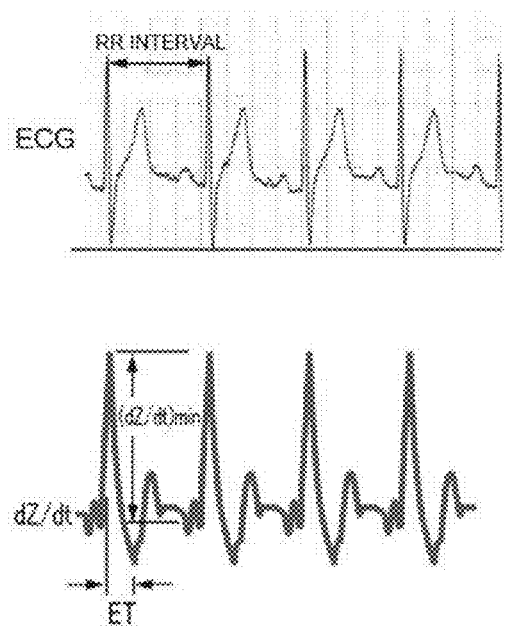
FIG. 2B is a diagram showing an ECG and a waveform of thoracic impedance dZ/dt.

FIG. 2B shows a waveform of continuous electrocardiogram and dZ/dt of thoracic impedance. The heart contracts and dilates between R waves in the electrocardiogram waveform, and blood is ejected. An interval between R waves is called an RR interval. As shown in FIG. 2B, when the heart remains in regular normal rhythm, namely, sinus rhythm, beat-to-beat intervals (RR intervals) are held constant, and the (dZ/dt)min of thoracic impedance also shows constant value.

Figure 2C:
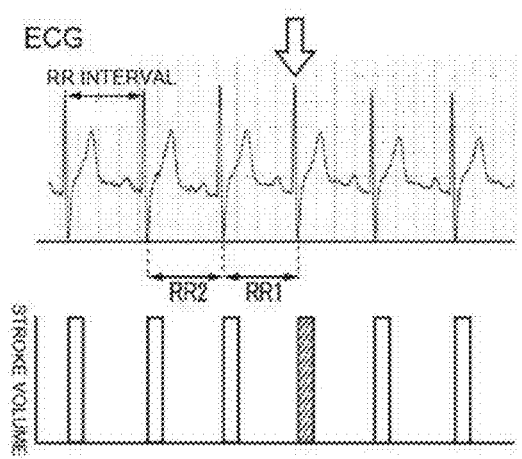
FIG. 2C shows a relationship between an ECG and a stroke volume in sinus rhythm.

The amount of blood ejected from the heart, that is, a stroke volume, is affected by the length of an RR interval preceding the R wave. FIG. 2C schematically shows a stroke volume when the heart remains in sinus rhythm. An RR interval preceding the R wave indicated by an arrow is called a preceding RR interval (RR1), and an RR interval further preceding it is called a pre-preceding RR interval (RR2). FIG. 2C schematically shows that the length of RR1 preceding the R wave indicated by the arrow relates to the corresponding stroke volume (shown by hatching). When RR1 is constant, that is, when the heart remains in sinus rhythm, the stroke volume is also constant.

Figure 2D:
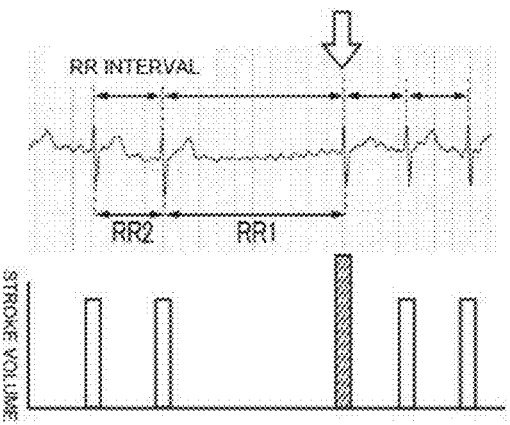
FIG. 2D shows a relationship between an ECG and a stroke volume in atrial fibrillation.

However, in atrial fibrillation, the RR intervals are irregular. FIG. 2D shows an electrocardiogram (ECG) in a patient with atrial fibrillation. It is apparent that the RR intervals are not constant and the cardiac cycle is irregular.

In general, when the preceding RR interval (RR1) is long, diastole is prolonged and the duration of blood flow from atria to ventricles increases. Consequently, the amount of blood filling the ventricles increases, and the amount of blood ejected during systole also increases. On the other hand, when the preceding RR interval is short, the diastole is shortened and the duration of blood flow from atria to ventricles decreases. Therefore, the amount of blood filling the ventricles decreases, and the amount of blood ejected during systole also decreases.

As shown in FIG. 2D, when atrial fibrillation occurs, the RR intervals are irregular. The length of the RR1 interval preceding the R wave indicated by the arrow is longer than other RR intervals, so that the corresponding stroke volume (shown by hatching) also increases.

The inventor of the present invention has found that in the dZ/dt waveform of the first derivative of thoracic impedance in cardiac function, there is a good correlation between (dZ/dt)min representing the peak flow velocity of blood ejected from the ventricles and the preceding RR interval (RR1). When displayed by applying RR1 to a horizontal axis and (dZ/dt)min to a vertical axis, it is possible to exhibit a graph reflecting the cardiac function in patients.

FIG. 3 shows a case measured by the device of the present invention. FIGS. 3A and 3B display thoracic impedance data of the patient with heart failure before and after treatment, by the two-dimensional scatter plot and the approximate curve (ventricular function curve) created by the (dZ/dt)min method of the present invention. FIGS. 3C and 3D use the thoracic impedance data identical to that of FIGS. 3A and 3B, and display them by the two-dimensional scatter plot and the approximate curve (ventricular function curve) created by the SV method using the coordinates of stroke volume (SV) and the corresponding RR1 values, which is the conventional method for evaluating cardiac function.

The SV method is that stroke volume (SV) is calculated from measurement values obtained by the thoracic impedance method, according to the following Kubicek formula.

$$SV = \rho (L/Zo)^2 (dZ/dt)\text{min} \times ET$$

(ρ: blood resistivity (Ω×cm), ET: left ventricular ejection time (sec), L: distance between electrodes, Zo: thoracic baseline impedance)

As shown in FIG. 3A, the set of measurement points displayed a V-shaped pattern on the two-dimensional scatter plot using the coordinates of RR1 and (dZ/dt)min values. This is the plotted image often observed in the period of exacerbation of heart failure, which has been found by the analytical method of the present invention. Further, the plotted image showing a characteristic belt-like pattern extending vertically in the RR intervals ranging from 400 to 500 ms is the set of points mainly representing Frank-Starling mechanism and mechanical restitution, which do not function sufficiently (described below).

FIG. 3B is a graph obtained by the analytical method of the present invention after treatment. The plotted image showing a typical belt-like pattern extending vertically in the RR intervals ranging from 400 to 500 ms, which is observed in the period of exacerbation of heart failure before treatment as shown in FIG. 3A, has disappeared, and it is found that the slope of the approximate curve (ventricular function curve) calculated from the measurement points is largely changed. As presented above, it is apparent that when data is plotted using the method of the present invention, distribution patterns of two-dimensional data differ depending on the stage of the disease. Accordingly, it is possible to assess the condition of the disease by using distribution patterns of two-dimensional data as an index.

On the other hand, in the conventional SV method, no large difference is found in the shape of a set of measurement points and the approximate curve (ventricular function curve), even when comparing FIG. 3C displaying data before treatment with FIG. 3D displaying data after treatment. Thus, it is difficult to determine the therapeutic effect.

As presented above, the (dZ/dt)min method of the present method makes it possible to evaluate small changes sensitively in cardiac function caused by treatment and the like, compared to the conventional SV method for the observation of cardiac function in atrial fibrillation.

Next, details of the measurement method and the device will be described. It should be noted that the device of the present invention is not limited to embodiments described below, and any devices are allowed to use if thoracic impedance and ECG can be measured simultaneously.

<Measurement Device>

Figure 4A:
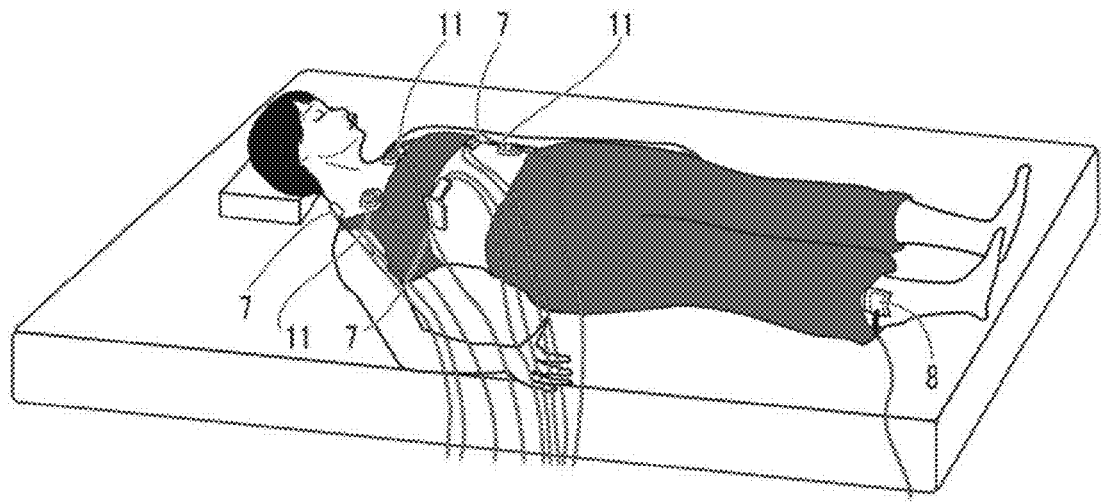
FIG. 4A is an illustration showing an arrangement of electrodes of a cardiac function measurement and evaluation device of the present invention.
Figure 4B:
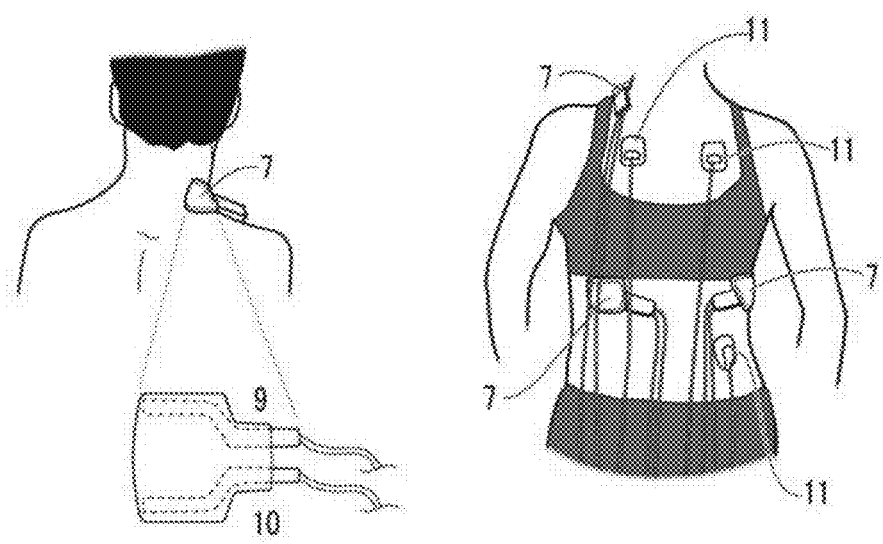
FIG. 4B is an illustration showing an arrangement of electrodes, on the chest, of the cardiac function measurement and evaluation device of the present invention.

The device of the present invention requires measuring impedance and ECG simultaneously. Therefore, electrodes for measuring impedance and ECG are applied to a subject (FIG. 4).

An Impedance measurement electrodes 7 is attached to the back of the neck and two of them are attached to the right and left front sides of the thorax at the height of the xiphoid process in the patient. Further, a neutral electrode 8 is attached to an ankle. As the impedance measurement electrode 7, one having any shape may be used if a drive electrode 9 for applying an electrical current and a receive electrode 10 for measuring the impedance are paired. A thoracic impedance measuring unit applies an electrical current from the drive electrode 9 to the patient by the isolation power supply, detects electrical signals generated by the pulsation using the receive electrode 10, and records them.

ECG measurement electrodes 11 are placed on the right and left sides of the chest and the left abdominal side. Here, while the device for measuring ECG using three leads placing electrodes at three points is described as an example, methods using any kind of leads allow for measuring the ECG.

As an impedance measuring unit 2 and a ECG measuring unit 3, publicly known ones of any measurement forms may be used if thoracic impedance and ECG can be measured, respectively, at the same time. Further, by means of miniaturizing the device itself, that can be also used as a portable device depending on requirements.

Figure 5:
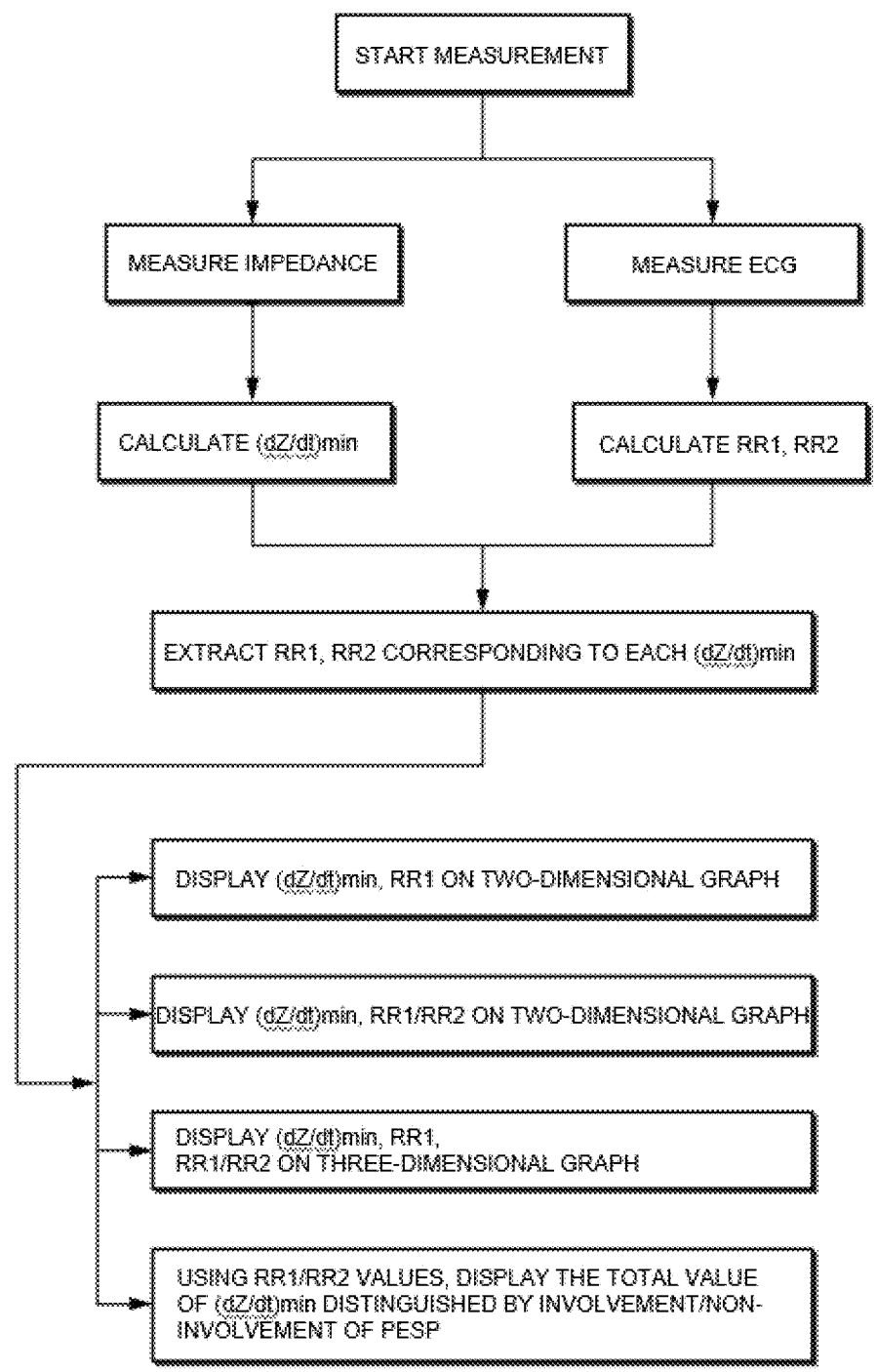
FIG. 5 is a flowchart showing operation of the cardiac function measurement and evaluation device.

FIG. 5 shows the outline of a measurement method. Continuous sets of impedance data and ECG data are obtained by starting measurement of impedance and ECG simultaneously. While 500 heartbeats are recorded in the case shown in FIG. 3, heartbeats to be measured may be any number if it is statistically reliable. In general, when recording 500 beats, the time required for measurement is about 7 to 10 minutes.

Then, (dZ/dt)min values are calculated from the measured thoracic impedance data, and RR1 values are calculated from ECG data of the corresponding beats. A two-dimensional scatter plot is created by plotting points representing RR1 values for X-axis coordinates and (dZ/dt)min values for Y-axis coordinates. Further, an approximate curve (a logarithmic curve) of the set of points is also obtained. The examples measured and displayed by the device of the present invention in this way are shown as FIGS. 3A and 3B described above.

Furthermore, by using various displays as described below, cardiac function in patients can be distinguishably evaluated by the mechanisms, namely Frank-Starling mechanism (FSM), mechanical restitution (MR), and postextrasystolic potentiation (PESP).

As shown in FIGS. 3A and 3B, when cardiac function is analyzed by the (dZ/dt)min method using the device of the present invention and displayed as a two-dimensional scatter plot, the plot can be classified into some typical sets of measurement points, according to the state of cardiac function. FIG. 6 schematically shows typical conditions of heart disease.

FIG. 6A shows a typical pattern of a set of measurement points in a condition of heart failure with atrial fibrillation. The set of points shows a V-shaped pattern. FIG. 6B schematically shows a typical distribution pattern of measurement points in a patient with atrial fibrillation and well preserved cardiac function. When the cardiac function is improved, the distribution pattern shifts from the set of measurement points displaying a V-shaped pattern to a form of parabola extending in a right-upward direction. In addition, since a tendency of tachycardia is improved, and the RR interval is increased, the measurement points scatter in a wide range in the X-axis direction.

FIG. 6C schematically shows a set of measurement points in sinus rhythm. Since RR intervals are almost constant in sinus rhythm, measurement points are concentrated in a small area. As described above, it is possible to determine the state of cardiac function only from distribution patterns of measurement points. Use of the device of the present invention makes it possible to evaluate cardiac function visually and determine the cardiac function without requiring skill.

Further, by allowing a storage unit to store typical patterns and allowing a determination module provided in the arithmetic unit, to compare a distribution pattern of measurement points of a patient with the stored patterns, it is also possible to allow the device to determine the state of cardiac function. Since plotted patterns differ in the condition of the disease as described above, the determination module is capable of diagnosing the condition of the disease by comparing a plot pattern of a subject with the typical patterns stored in the storage unit.

<Application of Display Method>

Next, applied examples of a display method using the device of the present invention will be described. Three mechanisms, namely Frank-Starling mechanism (FSM), mechanical restitution (MR), and postextrasystolic potentiation (PESP) are known as ventricular contractile mechanisms. Using a cardiac function measurement and evaluation device of the present invention also makes it possible to easily perform analysis with respect to these mechanisms, so that cardiac function can be considered in detail.

(1) Displaying Simultaneously on a Two-Dimensional Graph

Ventricular contractile mechanisms include Frank-Starling mechanism (FSM), mechanical restitution (MR), both of which depend on the length of preceding RR interval (RR1), and postextrasystolic potentiation (PESP) which depends on the length of pre-preceding RR interval (RR2).

FSM and MR are mechanisms in which ventricular contractile force increases as the preceding RR interval (RR1) increases. FSM and MR are phenomena that have been observed in an experimental model in which ventricular volume in FSM varies, while ventricular volume in MR is constant. In the case of a natural-heart of a human, FSM and MR are handled together (FSM+MR action) because of the difficulty in clinically distinguishing them from each other. It is known that the slope of the FSM+MR curve represents the degree of action of three factors, namely preload, afterload, and myocardial contractility.

On the other hand, PESP is the mechanism in which ventricular contractile force increases as the pre-preceding RR interval (RR2) is shorter than RR1. It is known that the slope of the regression line of PESP representing the correlation between the ratio of RR1/RR2 (where RR1/RR2>1 under the definition of PESP) and the ventricular contractile force reflects the degree of sympathetic nerve activity.

Using the cardiac function measurement and evaluation device of the present invention makes it possible to use for treatment by obtaining the FSM+MR curve not involved in PESP, and the PESP+FSM+MR curve involved in PESP. The (dZ/dt)min values corresponding to RR2 equal to or greater than RR1, i.e., RR1/RR2≤1 and (dZ/dt)min values corresponding to RR2 less than RR1, i.e., RR1/RR2>1 are extracted from the thoracic impedance data obtained from a patient.

Extracting data corresponding to RR1/RR2≤1 is capable of extracting (dZ/dt)min values not involved in PESP. Accordingly, a graph plotting the data reflects Frank-Starling mechanism and mechanical restitution, and an approximate curve (a logarithmic curve, FSM+MR curve) fitted to the set of such points also represents the Frank-Starling mechanism and the mechanical restitution.

On the other hand, RR1/RR2>1 shows that RR2 is shorter than RR1, which represents postextrasystolic potentiation (PESP). Therefore, when extracting (dZ/dt)min values corresponding to RR1/RR2>1 as a data set and plotting the data, the set of such points indicates the set of points involved in PESP, so that an approximate curve (a logarithmic curve, PESP+FSM+MR curve) fitted to the set of such points reflects involvement of PESP.

By using data in the patient with exacerbation of heart failure and atrial fibrillation shown in FIG. 3, FSM+MR and PESP+FSM+MR before and after treatment are obtained by using a relational expression between RR1 and RR2, and are shown as displaying simultaneously on the two-dimensional graphs, according to the method described above (FIGS. 7A and 7B).

Gray points show measurement values associated with the Frank-Starling mechanism and the mechanical restitution (FSM+MR), and black points show values associated with involvement of postextrasystolic potentiation (PESP) in addition to FSM+MR. Further, a dotted line represents an approximate curve fitted to the set of points associated with FSM+MR, and a solid line represents an approximate curve fitted to the set of points associated with PESP+FSM+MR.

The plotted patterns and the approximate curves apparently differ between before treatment (A) and after treatment (B). Before treatment of heart failure, the action of FSM+MR mechanism does not fully function, because tachycardia caused by sympathetic nerve hyperactivity leads to shortened ventricular diastolic time (RR1). Consequently, the slope of the FSM+MR curve decreases, which reflects a decrease in ventricular contractility. However, the slope of the PESP+FSM+MR curve involved in PESP is maintained compared to that of the FSM+MR curve, because of the enhanced action of PESP mechanism caused by sympathetic nerve hyperactivity in the early stage of heart failure.

In contrast, after treatment of heart failure, improvement in tachycardia and thereby prolonging ventricular diastolic time (RR1) reflect an increase in ventricular contractility caused by the action of FSM+MR mechanism. Accordingly, the slope of the FSM+MR curve shows a significant increase. Then, the slope of the PESP+FSM+MR curve involved in FSM+MR also shows a further increase from that observed before treatment.

As described above, using the device of the present invention makes it possible to display measurement values associated with Frank-Starling mechanism and mechanical restitution (FSM+MR), measurement values associated with PESP+FSM+MR involved in postextrasystolic potentiation (PESP) in addition to FSM+MR, and an FSM+MR curve and a PESP+FSM+MR curve, both of which represent each approximate curve. Therefore, it is able not only to visually determine the cardiac function, but also to analyze and evaluate the treatment effects in more detail.

(2) Displaying the Total Values of FSM+MR, PESP+FSM+MR

Using only pattern of the set of points in which RR1 values are plotted on the horizontal axis and (dZ/dt)min values are plotted on the vertical axis, and changes in the correlation between approximate curves, it is difficult to assess the degree of involvement of respective FSM+MR and PESP+FSM+MR mechanisms, in the recovery process of cardiac function.

Therefore, in a total of 500 heartbeats of obtained thoracic impedance data, the total value of (dZ/dt)min values corresponding to $RR1/RR2 \leq 1$ (total value of FSM+MR) and the total value of (dZ/dt)min values corresponding to $RR1/RR2 > 1$ (total value of PESP+FSM+MR) are calculated, and displayed as distinguishable bar graphs. The degree of involvement of respective FSM+MR and PESP+FSM+MR mechanisms are quantitatively represented, before and after the treatment (FIG. 7C).

In the case shown in FIG. 7, it is recognized that PESP+FSM+MR involved in PESP is greatly involved in the recovery of cardiac function after treatment, compared with FSM+MR. This graph shows that administration of β-blocker for suppressing sympathetic nerve activity and often used for improving tachycardia without careful consideration may lead to suppression of PESP action, which may make the cardiac function worse.

As described above, by means of obtaining a total of (dZ/dt)min values of FSM+MR and PESP+FSM+MR, the degree of contribution of pathophysiological mechanisms in the recovery process of cardiac function can be assessed, which cannot be estimated only from changes in the correlation between plotted patterns and approximate curves of the sets of respective measurement values shown in the two-dimensional simultaneous display graphs in which RR1 and (dZ/dt)min values constitute coordinates. Then, selection of drugs and the administration period can be determined according to the objective data in addition to subjective symptoms in patients.

(3) Displaying Simultaneously on a Three-Dimensional Graph.

Since a two-dimensional graph displaying FSM+MR and PESP+FSM+MR simultaneously as shown in FIG. 7 is a plane graph, there are some dots which is hard to evaluate visually due in part to overlap of dots representing FSM+MR and PESP+FSM+MR. Therefore, displaying them simultaneously on a three-dimensional scatter plot makes it possible to separate overlapping dots and thereby to display them in a manner capable of being evaluated visually and more easily (FIG. 8).

By using a total of 500 heartbeats of thoracic impedance data obtained from a patient with atrial fibrillation, preceding RR interval (RR1) values, pre-preceding RR interval (RR2) values, and RR1/RR2 values are obtained. Then, (dZ/dt)min values corresponding to RR1 when $RR1/RR2 > 1$ are extracted as (dZ/dt)min values associated with Frank-Starling mechanism (FSM) and mechanical restitution (MR) involved in postextrasystolic potentiation (PESP), (PESP+FSM+MR), and (dZ/dt)min values corresponding to RR1 when $RR1/RR2 \leq 1$ are extracted as (dZ/dt)min values associated with Frank-Starling mechanism (FSM) and mechanical restitution (MR) not involved in postextrasystolic potentiation (FSM+MR). A three-dimensional simultaneous scatter plot is created by applying RR1 to X-axis, RR1/RR2 to Y-axis, and (dZ/dt)min to Z-axis, using RR1 and RR1/RR2 corresponding to the respective extracted (dZ/dt)min, and overlapping two types of data sets in a distinguishable manner.

Displaying simultaneously on a three-dimensional graph makes it possible to recognize the distribution of points representing PESP+FSM+MR and FSM+MR without any overlapping parts. Accordingly, it is possible to detect a slight change in cardiac function more accurately, and to provide very useful information for diagnosis of cardiac function in patients with atrial fibrillation and monitoring of treatment course.

FIG. 8 is a three-dimensional graph displayed simultaneously in the patient with mitral valve stenosis and chronic atrial fibrillation. Gray dots represent points associated with Frank-Starling mechanism (FSM) and mechanical restitution (MR), and black dots represent points involved in postextrasystolic potentiation (PESP) in addition to FSM+MR.

In the two-dimensional graph displayed simultaneously, dots of FSM+MR and PESP+FSM+MR partially overlap with each other. However, since the overlapping parts are separated in the three-dimensional graph, the distribution of dots can be recognized accurately. Therefore, slight changes in the distribution of dots before and after administration of drugs or caused by changes in disease conditions can be found easily, so that it is possible to provide more detailed information on cardiac function for diagnosis and treatment.

(4) Slope of FSM+MR Curve (Pediatric Respiratory Sinus Arrhythmia)

FIG. 9 shows a case of pediatric respiratory sinus arrhythmia. Respiratory sinus arrhythmia is a physiological phenomenon observed in children, in which heart rate increases during inspiration and decreases during expiration. FIG. 9A shows a two-dimensional scatter plot displayed simultaneously in which dots associated with Frank-Starling mechanism (FSM) and mechanical restitution (MR), (FSM+MR), and dots involved in postextrasystolic potentiation (PESP) in addition to FSM+MR are overlapped with each other. FIG. 9B shows an FSM+MR curve, and FIG. 9C shows a regression line of PESP ($RR1/RR2 > 1$ under the definition of PESP).

Comparing these analytical results with results in patients with atrial fibrillation, it is characterized that the slope of an approximate expression obtained from the FSM+MR curve of the present case of a healthy child is 2.6, which is greater than 2.0. Regarding patients with atrial fibrillation except for hyperthyroidism, no matter how cardiac function is improved, the slope will never exceed 2.0. Therefore, when applying a value of 2.0 being used as a cut-off value, it is possible to early detect pediatric heart disease by using a coefficient value of the slope of the FSM+MR curve. This can be widely used for examination of cardiac function in children who are not able to explain subjective symptoms in words. Using this examination of cardiac function in preschool children may lead to early detection of heart disease in children.

Furthermore, the present method can be used for evaluating cardiac function of not only abnormal sinus arrhythmia but also sinus arrhythmia with bradycardia which is often observed in athletes in addition to pediatric respiratory sinus arrhythmia described above.

As described above, using the device of the present invention makes it possible to measure cardiac function noninvasively in patients with atrial fibrillation and to also analyze cardiac function in detail in various subjects such as children and athletes.

Because of the noninvasiveness of the device of the present invention, it is possible to evaluate and measure cardiac function with less burden on patients. Since cardiac function can be measured repeatedly in patients with atrial fibrillation to whom it was difficult to evaluate cardiac function noninvasively, not only diagnosis but also selection of treatment methods, the confirmation of treatment effect, and the like can be performed based on objective data.

REFERENCE SIGNS LIST 1 device for measurement and evaluation of cardiac function
7 impedance measurement electrode
8 neutral electrode
9 drive electrode
10 receive electrode
11 ECG measurement electrode

The invention claimed is:

1. A cardiac function measurement and evaluation that is a device for measuring and evaluating cardiac function in a subject, the device comprising:
   a thoracic impedance measuring unit;
   an electrocardiogram measuring unit;
   an arithmetic unit;
   a storage unit; and
   a display unit,
   wherein
   the thoracic impedance measuring unit includes drive electrodes for applying an electrical current, and receive electrodes for extracting an impedance signal, and measures a plurality of continuous sets of thoracic impedances,
   the electrocardiogram measuring unit includes a signal detection module that detects electrocardiogram signals from electrodes applied to the subject, and measures a plurality of continuous sets of electrocardiogram signals,
   the arithmetic unit calculates $(dZ/dt)min$ values of the plurality of continuous sets of thoracic impedances measured by the thoracic impedance measuring unit, and preceding RR intervals (RR1), pre-preceding RR intervals (RR2), and RR1/RR2 values of continuous sets of electrocardiogram data from R waves of the electrocardiogram signal obtained by the electrocardiogram measuring unit,
   the storage unit stores, as a data set: a $(dZ/dt)min$ value of each of the sets of thoracic impedance data corresponding to an RR1 value, RR2 value, and RR1/RR2 value of each of the calculated plurality of continuous sets of electrocardiogram data,
   the display unit displays each of the $(dZ/dt)min$ values corresponding to at least one of the RR1 value, RR2 value, and RR1/RR2 value,
   $(dZ/dt)min$ values where $RR1/RR2 \leq 1$ are extracted as first $(dZ/dt)min$ values which correspond to values reflecting Frank-Starling mechanism and mechanical restitution in which postextrasystolic potentiation is not involved,
   $(dZ/dt)min$ values where $RR1/RR2 > 1$ are extracted as second $(dZ/dt)min$ values which correspond to values reflecting postextrasystolic potentiation, Frank-Starling mechanism, and mechanical restitution in which postextrasystolic potentiation is involved, and
   the respective $(dZ/dt)min$ values of the thoracic impedance data extracted as the first and second $(dz/dt)min$ values are distinguishably plotted as a scatter plot on the display unit, wherein respective $(dz/dt)min$ value is plotted as a Y axis of the scatter plot, and corresponding RR1 value is plotted as an X axis of the scatter plot.

2. The cardiac function measurement and evaluation device according to claim 1, wherein
   from the scatter plot of the respective $(dZ/dt)min$ values of the thoracic impedance data extracted as the first and second $(dz/dt)min$ values, respective approximate curves are obtained and are displayed.

3. The cardiac function measurement and evaluation device according to any one of claim 1, wherein
   the storage unit is allowed to store standard data, and
   the arithmetic unit includes a determination module that compares obtained data of the subject with the standard data and determines cardiac function.

4. The cardiac function measurement and evaluation device according to claim 3, wherein
   the determination module further performs comparison with past data of same subject stored in the storage unit, and determines the course of cardiac function.

5. A cardiac function measurement and evaluation device that is a device for measuring and evaluating cardiac function in a subject, the device comprising:
   a thoracic impedance measuring unit;
   an electrocardiogram measuring unit;
   an arithmetic unit;
   a storage unit; and
   a display unit,
   wherein
   the thoracic impedance measuring unit includes drive electrodes for applying an electrical current, and receive electrodes for extracting an impedance signal, and measures a plurality of continuous sets of thoracic impedances,
   the electrocardiogram measuring unit includes a signal detection module that detects electrocardiogram signals from electrodes applied to the subject, and measures a plurality of continuous sets of electrocardiogram signals,
   the arithmetic unit calculates $(dZ/dt)min$ values of the plurality of continuous sets of thoracic impedances measured by the thoracic impedance measuring unit, and preceding RR intervals (RR1), pre-preceding RR intervals (RR2), and RR1/RR2 values of continuous sets of electrocardiogram data from R waves of the electrocardiogram signal obtained by the electrocardiogram measuring unit,
   the storage unit stores, as a data set: a $(dZ/dt)min$ value of each of the sets of thoracic impedance data corresponding to an RR1 value, RR2 value, and RR1/RR2 value of each of the calculated plurality of continuous sets of electrocardiogram data,
   $(dZ/dt)min$ values where $RR1/RR2 \leq 1$ are extracted as first $(dZ/dt)min$ values which correspond to values reflecting Frank-Starling mechanism and mechanical restitution in which postextrasystolic potentiation is not involved, (dZ/dt)min values where RR1/RR2>1 are extracted as second (dZ/dt)min values which correspond to values reflecting Frank-Starling mechanism and mechanical restitution in which postextrasystolic potentiation is involved, and a total of the respective (dZ/dt)min values are calculated by the arithmetic unit, and the display unit displays the total (dZ/dt)min values as a bar graph.

6. The cardiac function measurement and evaluation device according to any one of claim 5, wherein
the storage unit is allowed to store standard data, and
the arithmetic unit includes a determination module that compares obtained data of the subject with the standard data and determines cardiac function.

7. The cardiac function measurement and evaluation device according to claim 6, wherein
the determination module further performs comparison with past data of same subject stored in the storage unit, and determines the course of cardiac function.

8. A cardiac function measurement and evaluation device that is a device for measuring and evaluating cardiac function in a subject, the device comprising:
a thoracic impedance measuring unit;
an electrocardiogram measuring unit;
an arithmetic unit;
a storage unit; and
a display unit,
wherein
the thoracic impedance measuring unit includes drive electrodes for applying an electrical current, and receive electrodes for extracting an impedance signal, and measures a plurality of continuous sets of thoracic impedances,
the electrocardiogram measuring unit includes a signal detection module that detects electrocardiogram signals from electrodes applied to the subject, and measures a plurality of continuous sets of electrocardiogram signals,
the arithmetic unit calculates (dZ/dt)min values of the plurality of continuous sets of thoracic impedances measured by the thoracic impedance measuring unit, and preceding RR intervals (RR1), pre-preceding RR intervals (RR2), and RR1/RR2 values of continuous sets of electrocardiogram data from R waves of the electrocardiogram signal obtained by the electrocardiogram measuring unit,
the storage unit stores, as a data set: a (dZ/dt)min value of each of the sets of thoracic impedance data corresponding to an RR1 value, RR2 value, and RR1/RR2 value of each of the calculated plurality of continuous sets of electrocardiogram data,
the display unit displays each of the (dZ/dt)min values corresponding to each of the RR1 value, RR2 value, and RR1/RR2 value,
(dZ/dt)min values where RR1/RR2≤1 are extracted as first (dZ/dt)min values which correspond to values reflecting postextrasystolic potentiation, Frank-Starling mechanism, and mechanical restitution in which postextrasystolic potentiation is not involved,
(dZ/dt)min value where RR1/RR2>1 are extracted as second (dZ/dt)min value which correspond to values reflecting postextrasystolic potentiation, Frank-Starling mechanism, and mechanical restitution in which postextrasystolic potentiation is involved, and respective (dZ/dt)min values of the thoracic impedance data extracted as the first and second (dZ/dt)min values are distinguishably plotted as a three-dimensional scatter plot on the display unit, wherein the respective (dZ/dt)min value is plotted as a value of a Z axis, corresponding RR1 value as a value of an X axis, and RR1/RR2 value as a value of a Y axis.

9. A cardiac function measurement and evaluation device that is a device for measuring and evaluating cardiac function in a subject, the device comprising:
a thoracic impedance measuring unit;
an electrocardiogram measuring unit;
an arithmetic unit;
a storage unit; and
a display unit,
wherein
the thoracic impedance measuring unit includes drive electrodes for applying an electrical current, and receive electrodes for extracting an impedance signal, and measures a plurality of continuous sets of thoracic impedances,
the electrocardiogram measuring unit includes a signal detection module that detects electrocardiogram signals from electrodes applied to the subject, and measures a plurality of continuous sets of electrocardiogram signals,
the arithmetic unit calculates (dZ/dt)min values of the plurality of continuous sets of thoracic impedances measured by the thoracic impedance measuring unit, and preceding RR intervals (RR1), pre-preceding RR intervals (RR2), and RR1/RR2 values of continuous sets of electrocardiogram data from R waves of the electrocardiogram signal obtained by the electrocardiogram measuring unit,
the storage unit stores, as a data set: a (dZ/dt)min value of each of the sets of thoracic impedance data corresponding to an RR1 value, RR2 value, and RR1/RR2 value of each of the calculated plurality of continuous sets of electrocardiogram data,
the display unit displays each of the (dZ/dt)min values as a scatter plot corresponding to each RR1/RR2 value,
(dZ/dt)min values where RR1/RR2>1 are extracted as first (dZ/dt)min values which correspond to values reflecting postextrasystolic potentiation, Frank-Starling mechanism, and mechanical restitution in which postextrasystolic potentiation is involved.

10. The cardiac function measurement and evaluation device according to claim 9, wherein
from the scatter plot of the respective (dZ/dt)min values of the thoracic impedance data extracted as the first (dZ/dt)min values, an approximate straight line is obtained and is displayed.

11. A cardiac function measurement and evaluation device that is a device for measuring and evaluating cardiac function in a subject, the device comprising:
a thoracic impedance measuring unit;
an electrocardiogram measuring unit;
an arithmetic unit;
a storage unit; and
a display unit,
wherein
the thoracic impedance measuring unit includes drive electrodes for applying an electrical current, and receive electrodes for extracting an impedance signal, and measures a plurality of continuous sets of thoracic impedances, the electrocardiogram measuring unit includes a signal detection module that detects electrocardiogram signals from electrodes applied to the subject, and measures a plurality of continuous sets of electrocardiogram signals, the arithmetic unit calculates $(dZ/dt)min$ values of the plurality of continuous sets of thoracic impedances measured by the thoracic impedance measuring unit, and preceding RR intervals (RR1), pre-preceding RR intervals (RR2), and RR1/RR2 values of continuous sets of electrocardiogram data from R waves of the electrocardiogram signal obtained by the electrocardiogram measuring unit, the storage unit stores, as a data set: a $(dZ/dt)min$ value of each of the sets of thoracic impedance data corresponding to an RR1 value, RR2 value and RR1/RR2 value of each of the calculated plurality of continuous sets of electrocardiogram data, and standard data the display unit displays each of the $(dZ/dt)min$ values corresponding to at least one of the RR1 value, RR2 value, and RR1/RR2 value, the arithmetic unit includes a determination module that compares obtained data of the subject with the standard data and determines cardiac function, and the determination module further performs comparison with past data of same subject stored in the storage unit, and determines the course of cardiac function.

* * * * *